(12) United States Patent
Wiedekind-Klein

(10) Patent No.: US 10,101,350 B2
(45) Date of Patent: Oct. 16, 2018

(54) TRANSPORT OF LIQUID CONTAINERS IN AN AUTOMATED ANALYZER

(71) Applicant: Siemens Healthcare Diagnostics Products GmbH, Marburg (DE)

(72) Inventor: Alexander Wiedekind-Klein, Cochem (DE)

(73) Assignee: SIEMENS HEALTHCARE DIAGNOSTICS PRODUCTS GMBH, Marburg (DE)

(*) Notice: Subject to any disclaimer, the term of this patent is extended or adjusted under 35 U.S.C. 154(b) by 0 days.

(21) Appl. No.: 15/643,460

(22) Filed: Jul. 6, 2017

(65) Prior Publication Data
US 2018/0011119 A1 Jan. 11, 2018

(30) Foreign Application Priority Data
Jul. 11, 2016 (EP) .................................. 16178767

(51) Int. Cl.
*G01N 35/00* (2006.01)
*G01N 35/02* (2006.01)
*G01N 35/04* (2006.01)

(52) U.S. Cl.
CPC ....... *G01N 35/0099* (2013.01); *G01N 35/025* (2013.01); *G01N 35/04* (2013.01); *G01N 2035/00277* (2013.01)

(58) Field of Classification Search
CPC .. G01N 35/025; G01N 35/04; G01N 35/0099; G01N 2035/00277
See application file for complete search history.

(56) References Cited

U.S. PATENT DOCUMENTS

| | | |
|---|---|---|
| 5,772,962 A | 6/1998 | Uchida et al. |
| 2011/0086432 A1 | 4/2011 | Herz et al. |
| 2011/0150609 A1 | 6/2011 | Ford et al. |
| 2016/0334431 A1 | 11/2016 | Noda et al. |

FOREIGN PATENT DOCUMENTS

| | | |
|---|---|---|
| DE | 19542337 A1 | 5/1997 |
| EP | 2308588 A2 | 4/2011 |
| JP | H02152790 A | 6/1990 |
| WO | WO 2015/111526 | 7/2015 |

OTHER PUBLICATIONS

European Search Report of European Application No. 16178767.6-1553 dated Jan. 31, 2017.

*Primary Examiner* — Benjamin R Whatley
(74) *Attorney, Agent, or Firm* — Dugan & Dugan, PC

(57) ABSTRACT

The invention relates to a device and a method for the transfer of a liquid container with the aid of a clamping gripper in an automated analyzer. For this purpose, the clamping gripper has a controllable expansion device.

6 Claims, 5 Drawing Sheets

TRANSPORT OF LIQUID CONTAINERS IN AN AUTOMATED ANALYZER

CROSS REFERENCE TO RELATED APPLICATION

This claims priority to European Patent Application No. EP 16178767.6, filed Jul. 11, 2016, which is hereby incorporated by reference herein in its entirety for all purposes.

FIELD

The present invention lies in the field of automated analyzers and relates to the transfer of liquid containers with the aid of a clamping gripper.

BACKGROUND

Current analyzers, as are used as a matter of routine in analytics, forensics, microbiology and clinical diagnostics, are able to carry out a multiplicity of detection reactions and analyses with a multiplicity of samples. In order to be able to carry out a multiplicity of examinations in an automated manner, various automatically operating devices for the spatial transfer of measuring cells, reaction containers and reagent liquid containers are required, such as transfer arms with a gripper function, transport belts or rotatable transport wheels, and devices for transferring liquids, such as pipetting devices. The analyzers comprise a central control unit which, by means of appropriate software, is able to largely independently plan and work through the work steps for the desired analyses.

Many of the analysis methods used in such analyzers operating in an automated manner are based on optical methods. Measurement systems based on photometric (e.g., turbidimetric, nephelometric, fluorometric, or luminometric) or radiometric measurement principles are particularly widespread. These methods permit the qualitative and quantitative detection of analytes in liquid samples without having to provide additional separation steps. The determination of clinically relevant parameters, for example, the concentration or the activity of an analyte, is often implemented by means of an aliquot of a bodily fluid of a patient being mixed simultaneously or in succession with one or more reagent liquids in a reaction vessel, as a result of which a biochemical reaction is set in motion, which brings about a measurable change in an optical property of the test preparation.

The measurement result is in turn forwarded to a memory unit by the measurement system and evaluated. Subsequently, the analyzer supplies a user with sample-specific measurement values by way of an output medium, such as a monitor, a printer, or a network connection.

For the spatial transfer of liquid containers, clamping grippers for grasping, holding, and releasing a liquid container are often provided, the clamping grippers being secured, by way of a flexible connecting element, on a horizontally and vertically movable transfer arm. EP-A2-2308588 describes an example of a device for transferring tube-shaped reaction vessels (cuvettes) within an automated analyzer. The device comprises a passive, elastically deformable gripper with two gripper arms for force-fit capture and holding of a liquid container and is suitable for receiving an individual cuvette placed in a receiving position, transporting the cuvette to a target position, and setting it down there in a further receiving position. Compared to active mechanical grippers, passive clamping grippers of this kind have the advantage of being relatively robust, by virtue of their simple design, and of requiring minimal maintenance.

The transport, described in EP-A2-2308588, of a liquid container with the clamping gripper basically comprises the following steps:

a) moving the clamping gripper horizontally in order to produce a clamped connection between the clamping gripper and the liquid container in a start position;

b) raising the clamping gripper in order to remove the liquid container from the start position;

c) moving the clamping gripper horizontally to a target position;

d) lowering the clamping gripper in order to position the liquid container in the target position; and e) moving the clamping gripper horizontally in order to release the clamped connection.

To receive or in other words take hold of a liquid container that stands upright in a receiving position (start position), the clamping gripper is moved laterally onto the liquid container by a horizontal movement of the transfer arm and is pressed against the liquid container until the clamping gripper opens and encloses the liquid container with force-fit engagement. By means of an upward movement of the transfer arm, the liquid container held by the clamping gripper is raised from the receiving position and can now be transported to any given target position in the analyzer, for example, to a receiving position in a measuring station. To set down or in other words release the liquid container in the target position, the liquid container is first of all lowered to the receiving position by a downward movement of the transfer arm, and the clamping gripper is drawn away laterally from the liquid container by a horizontal movement of the transfer arm. In this way, the liquid container is pressed against the inside wall of the receiving position and exerts a force on the clamping gripper, which finally opens and releases the liquid container.

A problem is that, when the cuvette is being received and being released, the lateral pressing on or pulling away of the gripper can have the effect that liquid splashes out of the cuvette, because the cuvette, during the pressing on or pulling away of the gripper, can at first tilt slightly in the receiving position and, when the gripper opens with a snap movement, is accelerated counter to the direction of travel of the gripper and strikes against the inside wall of the receiving position. Splashing liquid in the analyzer can lead to loss of liquid volume, to sensitive components being damaged, to liquid splashing into adjacent sample vessels or reaction vessels, thus causing distortion of measurement results, and also increased risk of infection of a user, particularly if the splashing liquid contains human or animal bodily fluids such as blood or urine.

To avoid such disturbances, the use of active gripper systems is known. U.S. Pat. No. 5,772,962 describes a gripping device with two gripper arms which are connected to each other via a tension spring. Moreover, an expansion device is provided which is able to press the gripper arms away from each other and thus control the gripping mechanism.

However, a disadvantage of active gripper systems is the high level of maintenance required, since the hundreds or even thousands of uses daily leads to rapid wear of the mechanical parts.

SUMMARY

Therefore, in an automated analyzer with a passive clamping gripper with two gripper arms for transporting liquid containers, the object of the invention is to improve the automated placement of liquid containers in receiving positions provided for them, such that splashing of liquid is avoided, without the solution according to the invention leading to excessive wear and onerous maintenance requirements.

According to the invention, the object is achieved by a controllable expansion device which is provided on the clamping gripper and which, in an active position, exerts a force on the gripper arms, such that the gripper arms are pressed away from each other, and which, in a passive position, does not exert a force on the gripper arms, and by the fact that this "active" gripper system is brought into use exclusively when a liquid container that contains a liquid volume is intended to be transferred.

This has the advantage that, when a liquid container that contains liquid is being received and/or released, the expansion device can be actuated such that the clamping force of the gripper can be briefly reduced. This prevents the snap movement during the production of the clamped connection between gripper and liquid container and, therefore, the splashing of liquid. During the transport of an empty liquid container, when there is no danger at all of liquid splashing out, the active actuation of the expansion device can be dispensed with and, therefore, the wear of the mechanical parts of the gripper system can be reduced.

Accordingly, the present invention relates to an automated analyzer comprising a first and a second receiving device, each with a multiplicity of receiving positions for liquid containers, and a device, which is secured on an automatically movable transfer arm, for transferring a liquid container from a receiving position on the first receiving device to a receiving position on the second receiving device. The device for transferring a liquid container comprises a passive clamping gripper with two gripper arms, between which a liquid container can be clamped by a horizontal movement of the gripper. The clamping gripper comprises a controllable expansion device which, in an active position, exerts a force on the gripper arms such that the gripper arms are pressed away from each other, and which, in a passive position, does not exert a force on the gripper arms.

The two-armed gripper can be designed in one piece and can be elastically deformable and substantially made of plastic or metal. The gripper is preferably in a tensioned state such that, as long as the expansion device is in the passive position and the gripper is pressed with sufficient force against a liquid container, there is a snap effect, and the gripper opens and engages around and secures the liquid container. Conversely, the gripper opens again and releases the liquid container only when the gripper is moved away with sufficient force from a fixed liquid container.

The expansion device is designed to be controllable. It can on the one hand adopt an active position, in which it exerts a force on the gripper arms, such that the gripper arms are pressed away from each other and are in a state of reduced tension. On the other hand, it can adopt a passive position in which it does not exert a force on the gripper arms.

In one embodiment, the expansion device comprises a drive shaft which protrudes perpendicularly between the two gripper arms of the gripper and at the end of which a pin-shaped expansion head is provided which, in the active position of the expansion device, is placed transversely in relation to the two gripper arms and thus exerts a pressing force on the gripper arms such that the gripper arms are pressed away from each other, and which, in the passive position of the expansion device, is placed longitudinally in relation to the two gripper arms and does not exert a force on the gripper arms.

Between the gripper arms there is preferably an opening or gap, the extent of which is adapted to the size of the liquid container that is to be transported. The length of the pin-shaped expansion head is preferably chosen such that, when the expansion device is placed transversely in the active position in relation to the two gripper arms, the ends of the expansion head touch the inside faces of the gripper arms and thus exert a pressing force on the gripper arms. The width of the pin-shaped expansion head is preferably chosen such that, when the expansion device is placed longitudinally in the passive position in relation to the two gripper arms, there is no contact between the expansion head and the inside faces of the gripper arms, such that no force is exerted on the gripper arms.

The expansion head is preferably connected to the end of the drive shaft via a connecting element, for example, via a connecting screw. Alternatively, the end of the drive shaft can be designed as a screw thread, onto which an expansion head with a matching internal thread is screwed.

In the simplest case, the expansion head can consist of a pin made of metal or plastic.

In a preferred embodiment, the expansion head has, at each of its two ends, a roller or ball mounted rotatably about a vertical axis. This has the advantage of reducing the frictional forces that arise when the expansion head is brought from the passive position to the active position by rotation of the drive shaft and the gripper arms are pressed apart. On the one hand, this reduces the force that is needed to move the drive shaft. On the other hand, it reduces the wear on the gripper arms, the expansion head, and the drive of the drive shaft. The roller or balls can be made of hard rubber, plastic or metal.

The drive shaft is preferably part of an actuator by means of which commands issuing from a control unit are converted into mechanical movement, particularly into a rotation of the drive shaft about its longitudinal axis. The actuator can be driven electrically or pneumatically, for example.

In another embodiment, the expansion device comprises a rod which can be inserted perpendicularly between the two gripper arms of the gripper and at the end of which a cone-shaped expansion device is provided which, in the active position of the expansion device, is inserted so deep between the gripper arms that it exerts a pressing force on the inside faces of the gripper arms, such that the gripper arms are pressed away from each other, and which, in the passive position of the expansion device, does not touch the two gripper arms and does not exert a force on the gripper arms.

The term "cone-shaped" in particular comprises circular cone and circular truncated cone geometries of the expansion head.

The end of the rod can be designed as a screw thread onto which the cone-shaped expansion head with a matching internal thread is screwed.

In the simplest case, the cone-shaped expansion head can be made of metal, plastic, or hard rubber. To reduce friction and to reduce the force applied when introducing the expansion head between the gripper arms, the surface is preferably coated with a material that aids sliding, for example, Teflon. Alternatively or in addition, one or more rollers or balls that are mounted rotatably about a horizontal axis in each case can be provided on the tapering flanks of the expansion head. This has the advantage of reducing the frictional forces that arise when the expansion head is brought from the passive position to the active position by a perpendicular movement of the rod and, therefore, the gripper arms are pressed away from each other. On the one hand, this reduces the force that is needed to move the rod. On the other hand, it reduces the wear on the gripper arms, the expansion head and the drive of the rod. The rollers or balls can be made of hard rubber, plastic, or metal.

The rod is preferably part of an actuator by means of which commands issuing from a control unit are converted into mechanical movement, particularly into a linear up and down movement along the longitudinal axis of the rod. The actuator can be driven electrically or pneumatically, for example.

If the expansion device comprises a drive shaft which protrudes perpendicularly between the two gripper arms of the gripper and at the end of which a pin-shaped expansion head is provided, the expansion device is brought from the active position to the passive position, and vice versa, by rotating the drive shaft about 90 degrees. For the change from the active position to the passive position, and vice versa, the rotation can either take place in 90 degree steps in one direction or else 90 degrees in one direction and then 90 degrees in the opposite direction.

If the expansion device comprises a rod which can be inserted perpendicularly between the two gripper arms of the gripper and at the end of which a cone-shaped expansion head is provided, the expansion device is brought from the passive position to the active position by perpendicular lowering of the rod. For the change from the active position to the passive position of the expansion device, the rod is raised perpendicularly.

In a preferred automated analyzer, the clamping gripper of the transfer device is connected to a horizontally and vertically movable transfer arm via a flexible connecting element. Moreover, the expansion device is preferably secured on the same transfer arm.

A "receiving position for a liquid container" denotes a site that is provided for the placement of a liquid container. This is often a structurally adapted receiving position which allows the liquid container to be safely stored upright, for example, sleeves in which a specifically configured liquid container can be inserted with form-fit engagement. In an automated analyzer, receiving positions are provided in the first instance for primary sample vessels, reaction vessels (usually in the form of transparent tubular cuvettes), and for reagent liquid containers. The receiving positions are located at defined positions, e.g., in movable receiving devices such as rotatable cuvette or reagent plates, or stationary storage containers.

A liquid container may for example be a primary sample vessel such as a blood sampling tube, which contains a liquid to be analyzed, or a reaction vessel, such as a transparent, tubular cuvette, in which a primary sample is mixed with the one or more reagents to form a reaction mix, which is then measured in a measurement station, or a reagent liquid container which contains a liquid which contains one or more substances for detection of one or more analytes. The reagent liquid container may furthermore be of multi-chamber form and may contain multiple different reagent liquids.

An automated analyzer according to the invention moreover comprises a control device which is configured such that it controls a method for transferring a liquid container with the following steps:

checking whether the liquid container to be transferred contains a volume of liquid or is empty; and (a) if it is established that the liquid container to be transferred is empty, the transfer is carried out as follows:
(i) moving the transfer device horizontally in order to produce a clamped connection between the clamping gripper (11) and the liquid container in the receiving position (4) of the first receiving device (5);
(ii) raising the transfer device in order to remove the liquid container from the receiving position (4);
(iii) moving the transfer device horizontally to a receiving position (14) of the second receiving device (15);
(iv) lowering the transfer device in order to position the liquid container in the receiving position (14) of the second receiving device (15); and
(v) moving the transfer device horizontally in order to release the clamped connection;
wherein the expansion device is located exclusively in the passive position during steps (a) (i) to (a) (v); and
(b) if it is established that the liquid container to be transferred contains a volume of liquid, the transfer is carried out as follows:
(i) moving the transfer device horizontally in order to produce a clamped connection between the clamping gripper (11) and the liquid container in the receiving position (4) of the first receiving device (5), wherein the expansion device (50, 60) is brought to the active position before the clamped connection is produced between the clamping gripper (11) and the liquid container, such that the expansion device exerts a force on the gripper arms (52, 62) and the gripper arms (52, 62) are forced away from each other;
(ii) raising the transfer device in order to remove the liquid container from the receiving position (4), wherein the expansion device (50, 60) is brought to the passive position before the transfer device is raised, such that the expansion device does not exert a force on the gripper arms (52, 62);
(iii) moving the transfer device horizontally to a receiving position (14) of the second receiving device (15);
(iv) lowering the transfer device in order to position the liquid container in the receiving position (14) of the second receiving device (15); and
(v) moving the transfer device horizontally in order to release the clamped connection, wherein the expansion device (50, 60) is brought to the active position before the transfer device is moved horizontally in order to release the clamped connection, such that the expansion device exerts a force on the gripper arms (52, 62) and the gripper arms (52, 62) are pressed away from each other.

The check as to whether the liquid container to be transferred contains a volume of liquid or is empty can be made in various ways. For example, a camera can be provided on the transfer device and monitors whether or not the liquid container to be transferred contains liquid. The check can also be made by the control device retrieving information from a data memory in which the filling state of a given liquid container is stored.

The advantages of the described invention and of its embodiments are in particular that already known passive gripper systems can be optimized by the arrangement of an expansion device, without the need for complicated modification of the gripper system per se. Since the expansion device can be actuated in order to improve the receiving and/or setting down of a liquid container but does not necessarily have to be replaced, the expansion device can be brought into use as and when required. For example, during the transfer of empty containers, when there is no danger of liquid splashing out, it is possible to dispense with an active use of the expansion device.

BRIEF DESCRIPTION OF THE DRAWINGS

The invention is explained below with reference to a drawing.

In detail.

Identical parts are denoted by the same reference signs in all of the figures.

DETAILED DESCRIPTION

Figure 1:
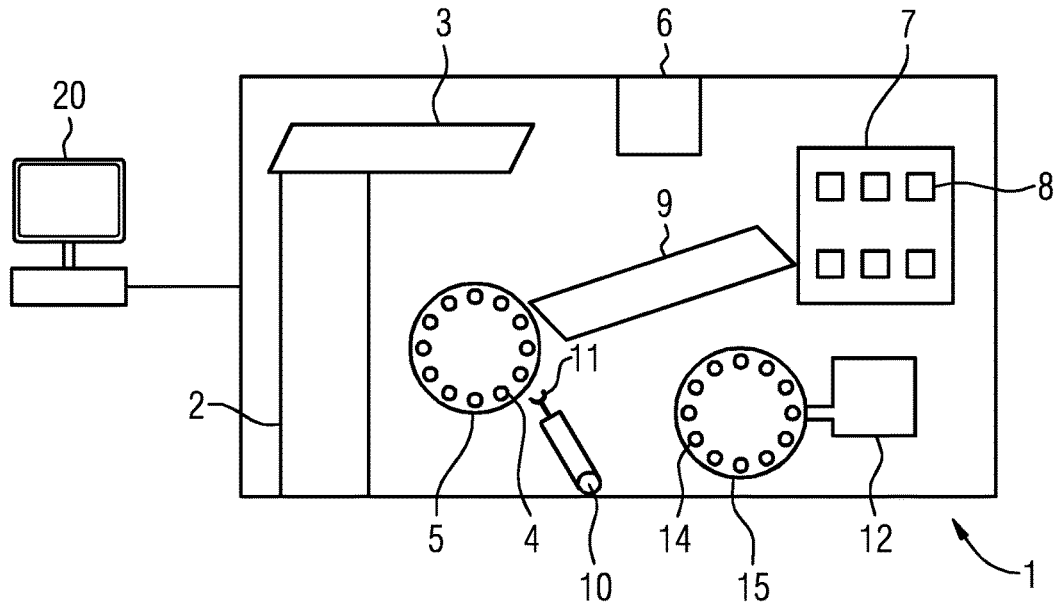
FIG. 1 shows an automated analyzer 1 according to the invention.

FIG. 1 is a schematic view of an automated analyzer 1 with some of the components contained therein. Here, only the most important components are illustrated, and in a much simplified manner, in order to explain the basic function of the automated analyzer 1 without depicting the individual parts of each component in detail.

The automated analyzer 1 is designed to carry out very different types of analyses of blood or other bodily fluids in a fully automated manner, without this requiring activity on the part of a user. Necessary interventions of a user instead are restricted to servicing or repairing and refill work, for example if cuvettes need to be refilled or liquid containers need to be replaced.

The patient samples are fed to the automated analyzer 1 via a feed track 2 on carriages not depicted in detail. Information concerning the analyses to be carried out for each sample may, for example, be transferred by means of barcodes which are attached to the sample vessels and which are read in the automated analyzer 1. With the aid of a first pipetting device 3, sample aliquots are removed from the sample vessels by means of a pipetting needle.

The sample aliquots are likewise fed to cuvettes (not depicted in any detail), which are arranged in receiving positions 4 of a rotatable incubation device 5 which is temperature-controlled to 37° C. The cuvettes are removed from a cuvette storage container 6. Reagent vessels 8 with various reagent liquids are stored in the reagent vessel storage container 7, which is cooled to approximately 8-10° C. Reagent liquid is taken from a reagent vessel 8 by means of the pipetting needle of a second pipetting device 9 and administered into a cuvette, which already contains a sample aliquot, for providing a reaction mix. By means of a transfer arm 10, the cuvette with the reaction mix is taken from the incubation device 5 by a clamping gripper 11 (having an expansion device not shown in detail) and transferred to a receiving position 14 of the rotatable receiving device 15 for the photometric measuring station 12, where the extinction of the reaction mix is measured.

Before the clamped connection is produced between the clamping gripper 11 and a liquid-containing cuvette in a receiving position 4, the expansion device is brought to the active position such that it presses the gripper arms of the clamping gripper away from each other. Before the clamping gripper 11 is raised, the expansion device is brought to the passive position such that it no longer exerts a force on the gripper arms, and the latter exert the full clamping force on the cuvette. After the clamping gripper 11 has been lowered in order to position the cuvette in a receiving position 14 of the measuring station 12, and before the clamping gripper 11 has been moved horizontally to release the clamped connection, the expansion device is brought to the active position such that it presses the gripper arms away from each other. In this way, when a cuvette filled with a reaction mix is being set down, an impulse of the cuvette occurring in the receiving position 14 is reduced and, consequently, splashing out of the liquid is avoided.

The entire process is controlled by a control unit 20, such as a computer connected by way of a data line, supported by a multiplicity of further electronic circuits and microprocessors (not shown in any detail) inside the automated analyzer 1 and its component parts.

Figure 2:
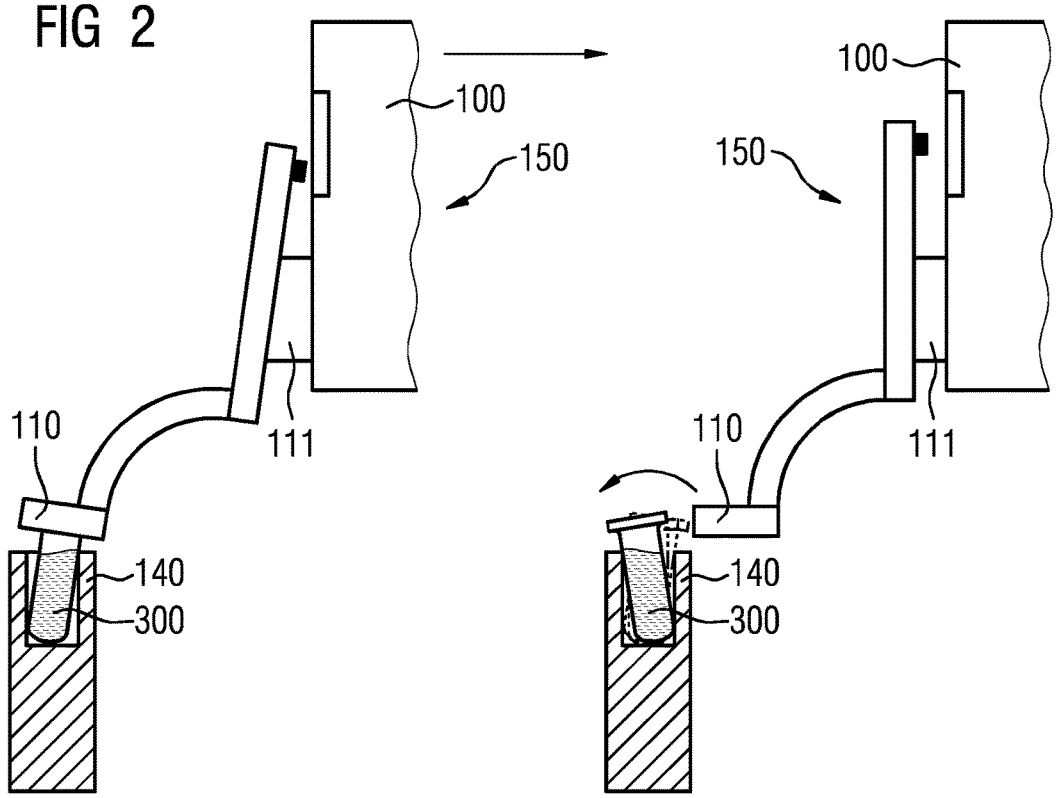
FIG. 2 shows the placement of a cuvette 300 according to the prior art.

FIG. 2 is a schematic view of the placement of a cuvette 300 in a receiving position 140 in an automated analyzer according to the prior art. The device 150 for transferring a cuvette 300 comprises a horizontally and vertically movable transfer arm 100, and a gripper 110 connected to the transfer arm 100 for the purpose of grasping, holding and releasing a cuvette. The gripper 110 is connected to the transfer arm 100 via a flexible intermediate element 111.

From left to right, the figure shows how the placing of the cuvette 300 in the receiving position 140 takes place in the prior art. After the cuvette 300 has first of all been lowered to the receiving position 140 by a downward movement of the transfer arm 100, the clamping gripper 110 is drawn away laterally from the cuvette 300 by a horizontal movement of the transfer arm 100 in the direction of the arrow. In this way, the cuvette 300 is pressed against the inside wall of the receiving position 140 and exerts a force on the clamping gripper 110, which finally opens and releases the cuvette 300. As is shown on the left, the cuvette 300 first of all tilts slightly as the clamping gripper 110 is pulled away and, when the clamping gripper 110 opens as shown on the right, the cuvette 300 is accelerated counter to the direction of movement of the gripper 110 and strikes against the inside wall of the receiving position 140. In this case there is the danger of reaction liquid splashing out of the cuvette 300.

Figure 3:
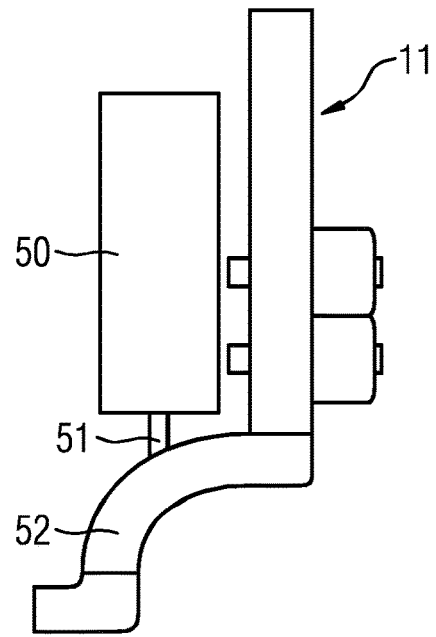
FIG. 3 shows a clamping gripper 11 according to the invention with an expansion device 50.

FIG. 3 shows a side view of a clamping gripper 11 with an expansion device 50. The drive shaft 51 of the expansion device 50 protrudes between the gripper arms 52.

Figure 4:
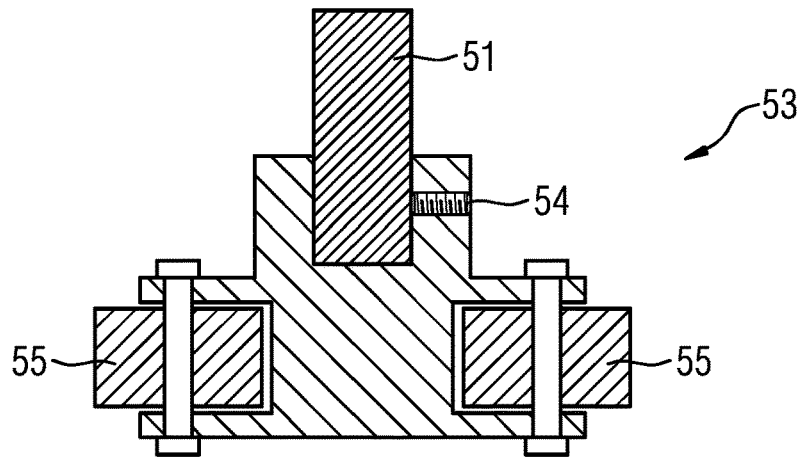
FIG. 4 shows the pin-shaped expansion head 53 of an expansion device 50 from the side.
Figure 5:
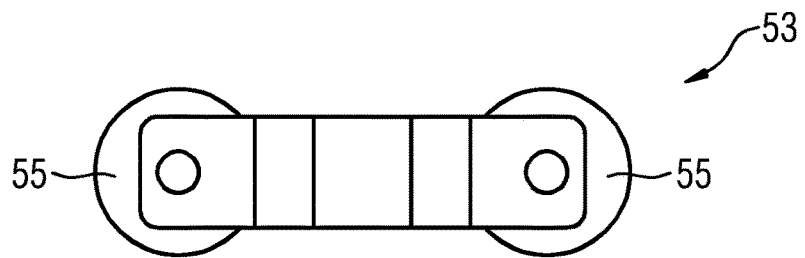
FIG. 5 shows the pin-shaped expansion head 53 of an expansion device 50 from above.

FIG. 4 shows a side view and FIG. 5 shows a plan view of an expansion head 53 of an expansion device 50. The expansion head 53 is secured by means of a screw 54 on the end of the drive shaft 51 of an electrically driven actuator (not shown). A rotatably mounted roller 55 made of hard rubber is provided at both ends of the expansion head 53.

Figure 6:
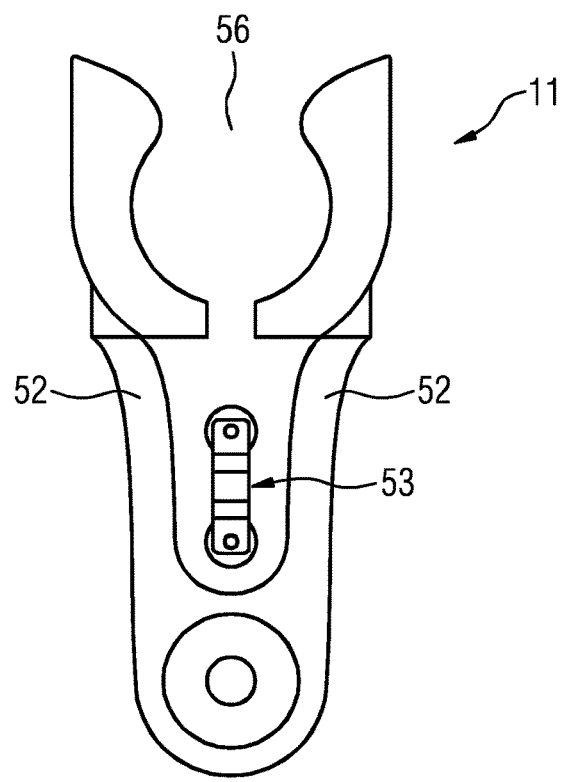
FIG. 6 shows a clamping gripper 11 with an expansion device 50 in the passive position.

FIG. 6 shows a plan view of a clamping gripper 11 with the expansion head 53 of an expansion device 50 in the passive position. The gripper arms 52 of the clamping gripper 11 are tensioned and form an opening 56 for clamping a circular cylindrical cuvette (not shown). The pin-shaped expansion head 53 is placed longitudinally in relation to the two gripper arms 52, such that there is no contact between the expansion head 53 and the inside faces of the gripper arms 52, with the result that no force is exerted on the gripper arms 52. The passive position, in which the clamping force of the clamping gripper 11 is at its highest, is set for example when a cuvette is located in the opening 56 and is transported horizontally or vertically.

Figure 7:
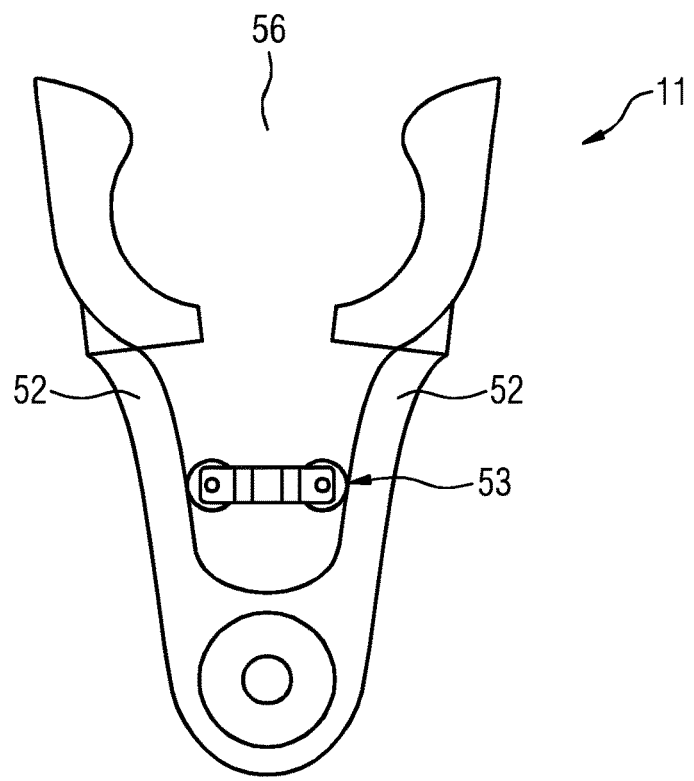
FIG. 7 shows a clamping gripper 11 with an expansion device 50 in the active position.

FIG. 7 shows a plan view of a clamping gripper 11 with the expansion head 53 of an expansion device 50 in the active position. The active position is reached when the expansion head 53 is rotated through 90 degrees. In this way, the expansion head 53 is placed transversely in relation to the two gripper arms 52. The ends of the expansion head 53 touch the inside faces of the gripper arms 52 and thus exert a pressing force on the gripper arms 52, which are thus pressed away from each other. In this way, the opening 56 is enlarged, such that the force that has to be overcome in order to receive or release a cuvette is reduced. The active position, in which the clamping force of the clamping gripper 11 is reduced, is set for example when a cuvette is located in the opening 56 and is to be set down at a target position and/or when a cuvette is intended to be clamped in the opening 56 at a start position.

Figure 8:
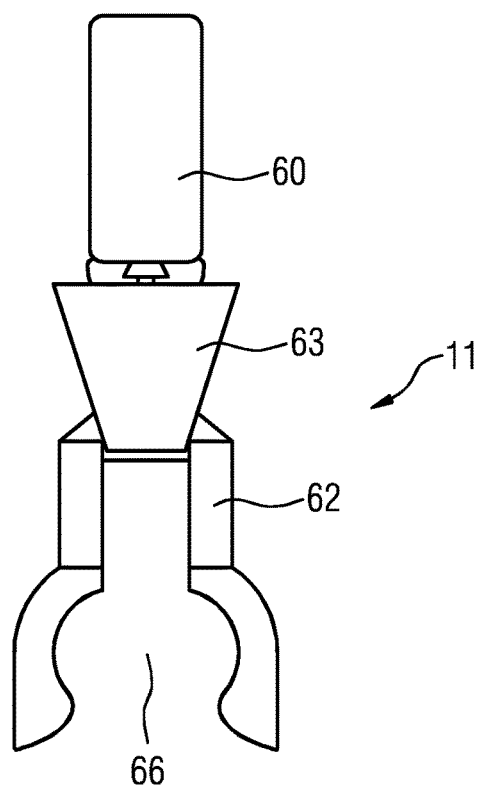
FIG. 8 shows an expansion device 60 with a frustoconical expansion head 63 in the passive position.
Figure 9:
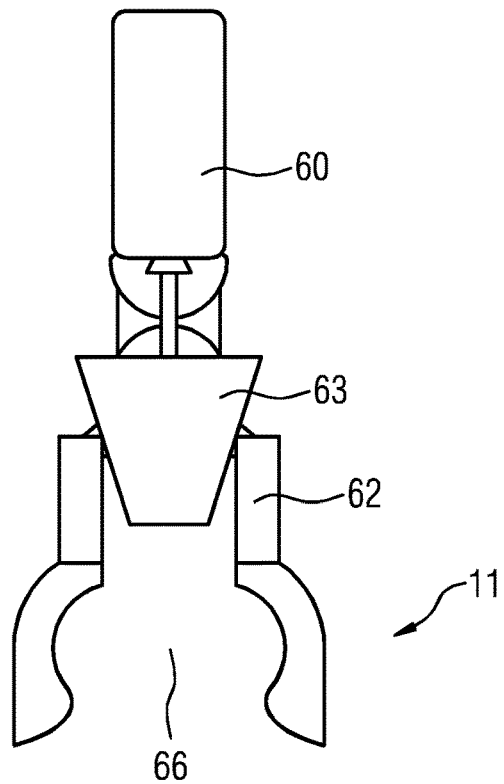
FIG. 9 shows an expansion device 60 with a frustoconical expansion head 63 in the active position.
Figure 10:
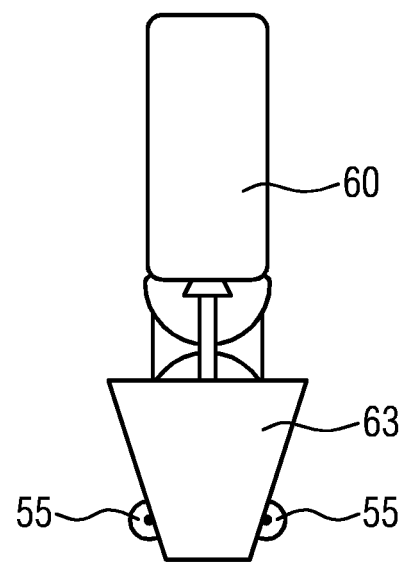
FIG. 10 shows an expansion device 60 with a frustoconical expansion head 63 having, on tapering flanks of the expansion head 63, one or more rollers or balls 55 that are mounted rotatably about a horizontal axis in each case.

FIGS. 8 and 9 show a front view of a clamping gripper 11 with the expansion head 63 of an expansion device 60 in the passive position (FIG. 8) and in the active position (FIG. 9). For the purposes of illustration, the arc-shaped portions of the gripper arms 62 are shown in a slightly different perspective than the rest of the device, i.e., more from above than from the front.

In the passive position (FIG. 8), the gripper arms 62 of the clamping gripper 11 are tensioned and form an opening 66 for clamping a circular cylindrical cuvette (not shown). The frustoconical expansion head 63 is located above the two gripper arms 62, such that there is no contact between the expansion head 63 and the inside faces of the gripper arms 62, with the result that no force is exerted on the gripper arms 62. The passive position, in which the clamping force of the clamping gripper 11 is at its highest, is set for example when a cuvette is located in the opening 66 and is transported horizontally or vertically.

The active position (see FIG. 9) is reached when the expansion head 63 is moved perpendicularly downward and inserted between the two gripper arms 62 of the clamping gripper 11. In this way, the jacket surfaces of the truncated cone touch the inside faces of the gripper arms 62 and thus exert a pressing force on the gripper arms 62, which are thus pressed away from each other. In this way, the opening 66 is enlarged, such that the force that has to be overcome in order to receive or release a cuvette is reduced. The active position, in which the clamping force of the clamping gripper 11 is reduced, is set for example when a cuvette is located in the opening 66 and is to be set down at a target position and/or when a cuvette is intended to be clamped in the opening 66 at a start position.

LIST OF REFERENCE SIGNS 1 analyzer
2 feed track
3 pipetting device
4 receiving position
5 incubation device
6 cuvette storage container
7 reagent vessel storage container
8 reagent vessel
9 pipetting device
10, 100 transfer arm
11, 110 clamping gripper
12 measuring station
14, 140 receiving position
15 receiving device
20 control unit
111 intermediate element
150 transfer device
300 cuvette
50, 60 expansion device
51 drive shaft
52, 62 gripper arm
53, 63 expansion head
54 screw
55 roller
56, 66 opening

What is claimed is:

1. An automated patient sample analyzer comprising:
a first and a second receiving device, each with a multiplicity of receiving positions for liquid containers, and a transfer device for transferring a liquid container from a receiving position on the first receiving device to a receiving position on the second receiving device, wherein the transfer device for transferring the liquid container comprises an automatically movable transfer arm and a passive clamping gripper with two gripper arms, between which the liquid container can be clamped by a horizontal movement of the clamping gripper, and wherein the clamping gripper comprises a controllable expansion device which, in an active position, exerts a force on the gripper arms such that the gripper arms are pressed away from each other, and which, in a passive position, does not exert a force on the gripper arms such that the gripper arms are tensioned in the passive position to engage and clamp the liquid container through a snap effect when the gripper arms are pressed against the liquid container,
wherein the expansion device comprises a rotating drive shaft which protrudes perpendicularly between the two gripper arms of the gripper and at an end of which an expansion head with a pin-shaped extension is provided which, in the active position of the expansion device, is rotated to be placed transversely in relation to the two gripper arms and exerts a pressing force on the inside faces of the gripper arms such that the gripper arms are pressed away from each other, and which, in the passive position of the expansion device, is rotated to be placed longitudinally in relation to the two gripper arms and does not contact or exert a force on the gripper arms,
wherein the automated analyzer further comprises a control device which is configured such that it controls a method with the following steps:
checking whether the liquid container to be transferred contains a volume of liquid or is empty; and
(a) upon determination that the liquid container to be transferred is empty, the transfer is carried out sequentially as follows:
(i) moving the transfer device horizontally to produce a clamped connection between the clamping gripper and the liquid container in the receiving position of the first receiving device;
(ii) raising the transfer device to remove the liquid container from the receiving position;

(iii) moving the transfer device horizontally to the receiving position of the second receiving device;
(iv) lowering the transfer device to position the liquid container in the receiving position of the second receiving device; and
(v) moving the transfer device horizontally to release the clamped connection;
wherein the expansion device is located exclusively in the passive position during steps (a) (i) to (a) (v); and
(b) upon determination that the liquid container to be transferred contains a volume of liquid, the transfer is carried out sequentially as follows:
(i) moving the transfer device horizontally to produce a clamped connection between the clamping gripper and the liquid container in the receiving position of the first receiving device, wherein the expansion device is brought to the active position before the clamped connection is produced between the clamping gripper and the liquid container, such that the expansion device exerts a force on the gripper arms and the gripper arms are pressed away from each other;
(ii) raising the transfer device to remove the liquid container from the receiving position, wherein the expansion device is brought to the passive position before the transfer device is raised, such that the expansion device does not exert a force on the gripper arms;
(iii) moving the transfer device horizontally to the receiving position of the second receiving device;
(iv) lowering the transfer device to position the liquid container in the receiving position of the second receiving device; and
(v) moving the transfer device horizontally to release the clamped connection, wherein the expansion device is brought to the active position before the transfer device is moved horizontally to release the clamped connection, such that the expansion device exerts a force on the gripper arms and the gripper arms are pressed away from each other.

2. The automated analyzer as claimed in claim 1, wherein the expansion head is connected to the end of the drive shaft via a connecting element.

3. The automated analyzer as claimed in claim 1, wherein the expansion head has, at each of its two ends, a roller or ball mounted rotatably about a vertical axis.

4. The automated analyzer as claimed in claim 1, wherein the drive shaft is part of an actuator.

5. An automated patient sample analyzer comprising:
a first and a second receiving device, each with a multiplicity of receiving positions for liquid containers, and a transfer device for transferring a liquid container from a receiving position on the first receiving device to a receiving position on the second receiving device, wherein the transfer device for transferring the liquid container comprises an automatically movable transfer arm and a passive clamping gripper with two gripper arms, between which the liquid container can be clamped by a horizontal movement of the clamping gripper, and wherein the clamping gripper comprises a controllable expansion device which, in an active position, exerts a force on the gripper arms such that the gripper arms are pressed away from each other, and which, in a passive position, does not exert a force on the gripper arms such that the gripper arms are tensioned in the passive position to engage and clamp the liquid container through a snap effect when the gripper arms pressed against the liquid container,
wherein the expansion device comprises a rod which can be inserted between the two gripper arms of the gripper and at an end of which a cone-shaped expansion head is provided which, in the active position of the expansion device, is inserted so deep between the gripper arms that it exerts a pressing force on the inside faces of the gripper arms, such that the gripper arms are pressed away from each other, and which, in the passive position of the expansion device, does not touch the two gripper arms and does not exert a force on the gripper arms,
wherein the automated analyzer further comprises a control device which is configured such that it controls a method with the following steps:
checking whether the liquid container to be transferred contains a volume of liquid or is empty; and
(a) upon determination that the liquid container to be transferred is empty, the transfer is carried out sequentially as follows:
(i) moving the transfer device horizontally to produce a clamped connection between the clamping gripper and the liquid container in the receiving position of the first receiving device;
(ii) raising the transfer device to remove the liquid container from the receiving position;
(iii) moving the transfer device horizontally to the receiving position of the second receiving device;
(iv) lowering the transfer device to position the liquid container in the receiving position of the second receiving device; and
(v) moving the transfer device horizontally to release the clamped connection;
wherein the expansion device is located exclusively in the passive position during steps (a) (i) to (a) (v); and
(b) upon determination that the liquid container to be transferred contains a volume of liquid, the transfer is carried out sequentially as follows:
(i) moving the transfer device horizontally to produce a clamped connection between the clamping gripper and the liquid container in the receiving position of the first receiving device, wherein the expansion device is brought to the active position before the clamped connection is produced between the clamping gripper and the liquid container, such that the expansion device exerts a force on the gripper arms and the gripper arms are pressed away from each other;
(ii) raising the transfer device to remove the liquid container from the receiving position, wherein the expansion device is brought to the passive position before the transfer device is raised, such that the expansion device does not exert a force on the gripper arms;
(iii) moving the transfer device horizontally to the receiving position of the second receiving device;
(iv) lowering the transfer device to position the liquid container in the receiving position of the second receiving device; and
(v) moving the transfer device horizontally to release the clamped connection, wherein the expansion device is brought to the active position before the transfer device is moved horizontally to release the clamped connection, such that the expansion device exerts a force on the gripper arms and the gripper arms are pressed away from each other.

6. The automated analyzer as claimed in claim 5, wherein the cone-shaped expansion head has, on tapering flanks of the cone-shaped expansion head, one or more rollers or balls that are mounted rotatably about a horizontal axis in each case.

* * * * *